United States Patent
Choi et al.

(10) Patent No.: US 10,908,582 B2
(45) Date of Patent: Feb. 2, 2021

(54) ELECTRONIC DEVICE FOR FOOD MANAGEMENT AND CONTROL METHOD THEREOF

(71) Applicant: Samsung Electronics Co., Ltd, Gyeonggi-do (KR)

(72) Inventors: Jun-hoe Choi, Hwaseong-si (KR); Tae-gyoon Noh, Suwon-si (KR); Seo-ho Lee, Seongnam-si (KR); Joo-young Ha, Suwon-si (KR); Ji-young Lee, Yongin-si (KR); Jeong-su Han, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 27 days.

(21) Appl. No.: 15/881,464

(22) Filed: Jan. 26, 2018

(65) Prior Publication Data
US 2018/0210418 A1      Jul. 26, 2018

(30) Foreign Application Priority Data
Jan. 26, 2017   (KR) ................ 10-2017-0012777

(51) Int. Cl.
| | | |
|---|---|---|
| *G05B 19/406* | (2006.01) | |
| *G01N 21/3563* | (2014.01) | |
| *G01N 21/359* | (2014.01) | |
| *G01N 33/02* | (2006.01) | |

(52) U.S. Cl.
CPC ......... *G05B 19/406* (2013.01); *G01N 21/359* (2013.01); *G01N 21/3563* (2013.01); *G01N 33/02* (2013.01); *G05B 2219/37426* (2013.01)

(58) Field of Classification Search
None
See application file for complete search history.

(56) References Cited

U.S. PATENT DOCUMENTS

| | | | |
|---|---|---|---|
| 2013/0010294 A1 | 1/2013 | Matsuda et al. | |
| 2015/0036138 A1* | 2/2015 | Watson | G01N 21/31 |
| | | | 356/402 |

FOREIGN PATENT DOCUMENTS

| | | |
|---|---|---|
| JP | 2006300810 A | 11/2006 |
| JP | 2012122680 A | 6/2012 |
| JP | 2014105933 A | 6/2014 |
| JP | 5845009 B2 | 1/2016 |
| KR | 100826715 B1 | 4/2008 |

* cited by examiner

*Primary Examiner* — Mohammad Ali
*Assistant Examiner* — Saad M Kabir

(57) ABSTRACT

Disclosed are an electronic device for food management and a control method thereof. A control method of an electronic device for food management includes measuring intensity of light, which is irradiated with food and reflected, by wavelengths using an infrared sensor; obtaining state information of the food based on the measured light intensity information; and adjusting at least one of temperature and humidity of an area where the food is disposed in the electronic device based on at least one of the obtained state information and preset usage plan information of the food. Accordingly, food which is managed in an optimal state in consideration of a state of a food stored in an electronic device and a using method (consumption period and consumption method) of the food can be provided to a user.

16 Claims, 10 Drawing Sheets

ELECTRONIC DEVICE FOR FOOD MANAGEMENT AND CONTROL METHOD THEREOF

CROSS-REFERENCE TO RELATED APPLICATION(S)

This application is related to and claims priority to Korean Patent Application No. 10-2017-0012777 filed on Jan. 26, 2017, the disclosure of which is incorporated by reference herein in its entirety.

TECHNICAL FIELD

Apparatuses and methods consistent with exemplary embodiments of the present disclosure relate to an electronic device for food management and a control method thereof and, more particularly, to an electronic device for managing a state of a food using an infrared sensor and a control method thereof.

BACKGROUND

With the development of technology, an electronic device such as a smart refrigerator automatically adjusts temperature and humidity of a storage room for storing food so that freshness of food can be maintained longer.

For example, the electronic device senses the temperature of a storage room for storing food, and when the sensed temperature is compared with a preset appropriate temperature, if the sensed temperature is higher than the appropriate temperature, the electronic device controls the temperature of the storage room to be maintained at an appropriate temperature level.

That is, a recently developed electronic device automatically adjusts the temperature and humidity of the storage room so that the temperature in the storage room of the electronic device or the storage room is maintained at a predetermined optimum temperature level.

In this case, the conventional electronic device has a problem that the temperature and humidity cannot be automatically adjusted in consideration of the condition of each food, although the entire temperature and humidity can be maintained in an appropriate temperature and humidity state.

Accordingly, there is a problem that the food stored in the storage room of the electronic device for a long time is spoiled to an extent that the user cannot eat.

SUMMARY

Exemplary embodiments address at least the above problems and/or disadvantages and other disadvantages not described above. Also, the exemplary embodiments are not required to overcome the disadvantages described above, and may not overcome any of the problems described above The present disclosure includes one or more exemplary embodiments that may address and/or solve the above-mentioned needs, and it is an object of the one or more exemplary embodiments of the present disclosure to enable a user to eat a food product which is managed in an optimal state in consideration of the state of food stored in an electronic device and the manner of use (eatable period and consuming method).

According to an exemplary embodiment, a control method of an electronic device for food management includes measuring intensity of light, which is irradiated with food and reflected, by wavelengths using an infrared sensor; obtaining state information of the food based on the measured light intensity information; and adjusting at least one of temperature and humidity of an area where the food is disposed in the electronic device based on at least one of the obtained state information and preset usage plan information of the food.

The adjusting may include, in response to a state of the food being a low grade based on the obtained state information, adjusting at least one of the temperature and the humidity so that the food can be stored for a long period of time.

The adjusting may include, in response to a state of the food being determined to be a low grade and the food being stored for a long time based on the use plan information, adjusting at least one of the temperature and the humidity so that long-term storage is available.

The adjusting may include, in response to the usage food information for long-term storage being input, adjusting at least one of the temperature and the humidity so that the food is able to be stored for a long time based on the state information of the food.

The adjusting may include, in response to use plan information for rapid ripening being input, adjusting at least one of the temperature and the humidity so that the food is able to be ripen within a period corresponding to use plan information for the rapid ripening.

The method further includes displaying a guide UI for the food on a screen based on the obtained state information, wherein the guide UI may include at least one of a first UI element for providing the food state and a second UI element for providing recipe information of the food.

The obtaining may include obtaining a state change model of the food from among a plurality of prestored state change models based on the measured light intensity information and obtaining the food state information by applying light intensity of a specific wavelength from among light intensities by wavelengths of the food to the obtained state change model.

The state change model may be a model which is generated by accumulating light intensities measured from wavelength of light which is reflected by irradiating the food with light through the infrared sensor in time units.

The obtaining may include transmitting the measured light intensity information to an external server and receiving the state information of the food determined based on the light intensity information from the external server.

The state information may include at least one of a type, ripening degree, and a content of nutrition of the food.

According to still another exemplary embodiment, an electronic device for food management includes a sensor configured to measure intensity of light, which is irradiated with food and reflected, by wavelengths using an infrared sensor; and a controller configured to obtain state information of the food based on the measured light intensity information and adjust at least one of temperature and humidity of an area where the food is disposed in the electronic device based on at least one of the obtained state information and preset usage plan information of the food.

The controller, in response to a state of the food being a low grade based on the obtained state information, may adjust at least one of the temperature and the humidity so that the food can be stored for a long period of time.

The controller, in response to a state of the food being determined to be a low grade and the food being stored for a long time based on the use plan information, may adjust at least one of the temperature and the humidity so that long-term storage is available.

The electronic device, in response to the usage food information for long-term storage being input, may adjust at least one of the temperature and the humidity so that the food is able to be stored for a long time based on the state information of the food.

The controller, in response to use plan information for rapid ripening being input, may adjust at least one of the temperature and the humidity so that the food is able to be ripen within a period corresponding to use plan information for the rapid ripening.

The device further includes a display, and the controller may control the display to display a guide UI for the food on a screen based on the obtained state information, wherein the guide UI may include at least one of a first UI element for providing the food state and a second UI element for providing recipe information of the food.

The device further includes a storage for storing a plurality of state change models by foods, wherein the controller may obtain a state change model of the food from among a plurality of prestored state change models based on the measured light intensity information and obtaining the food state information by applying light intensity of a specific wavelength from among light intensities by wavelengths of the food to the obtained state change model.

The state change model may be a model which is generated by accumulating light intensities measured from wavelength of light which is reflected by irradiating the food with light through the infrared sensor in time units.

The device further includes a communicator configured to perform data communication with an external server, wherein the controller may control the communicator to transmit the measured light intensity information to an external server and receive the state information of the food determined based on the light intensity information from the external server.

The state information may include at least one of a type, ripening degree, and a content of nutrition of the food.

As described above, according to the present disclosure, it is possible to provide a user with a food that is managed in an optimal state in consideration of the state of food stored in the electronic device and a manner of using the food (duration of ingestion and a method of ingestion).

Before undertaking the DETAILED DESCRIPTION below, it may be advantageous to set forth definitions of certain words and phrases used throughout this patent document: the terms "include" and "comprise," as well as derivatives thereof, mean inclusion without limitation, the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
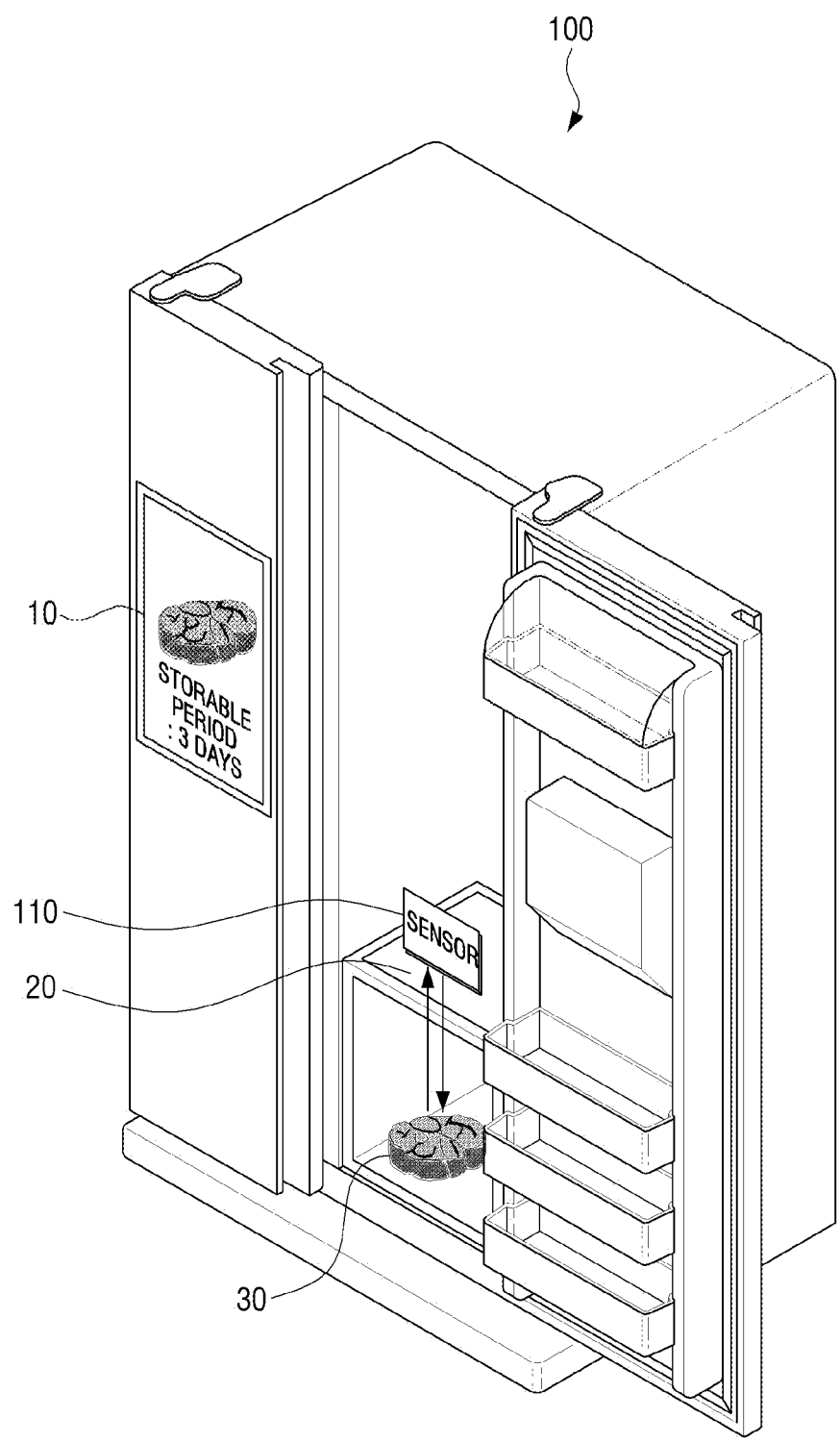
FIG. 1 is an exemplary view which illustrates a state of food in an electronic device according to an exemplary embodiment.

FIGS. 1 through 10, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments may be practiced without those specifically defined matters. Also, well-known functions or constructions are not described in detail since they would obscure the description with unnecessary detail.

The terms such as "first," "second," and so on may be used to describe a variety of elements, but the elements should not be limited by these terms. The terms are used only for the purpose of distinguishing one element from another.

A singular expression includes a plural expression, unless otherwise specified. It is to be understood that the terms such as "comprise" or "consist of" are used herein to designate a presence of characteristic, number, step, operation, element, component, or a combination thereof, and not to preclude a presence or a possibility of adding one or more of other characteristics, numbers, steps, operations, elements, components or a combination thereof.

In the example embodiments of the present disclosure, a 'module' or a 'unit' may perform at least one function or operation, and be implemented as hardware (e.g., circuitry) or software, or as a combination of hardware and software. Further, except for the 'module' or the 'unit' that has to be implemented as particular hardware (e.g., a dedicated processor), a plurality of 'modules' or a plurality of 'units' may be integrated into at least one module and implemented as at least one processor.

Hereinbelow, the present disclosure will be described in a greater detail with reference to the drawings.

FIG. 1 is an exemplary view which illustrates a state of food in an electronic device according to an exemplary embodiment.

As shown in FIG. 1, the electronic device 100 can be a food storage device such as a smart refrigerator, which can be stored so as not to deteriorate food.

The electronic device 100 may check the state of food in each area of the food storage area and automatically adjust the temperature and humidity of each area according to the state of the food in each area.

Specifically, as shown in FIG. 1, meat product 30 can be frozen and stored in a first area 20 of the electronic device 100, which is a smart refrigerator. The first area 20 in which the meat product 30 is stored may be provided with a sensor 110 for detecting the state of the meat product 30.

The sensor 110 provided on one side of the first area 20 irradiates light to the meat product 30 stored in the first area 20 by a predetermined unit of time (for example, in units of 24 hours). Here, the sensor 110 can irradiate the meat product 30 stored in the first area 20 with light using a near-infrared sensor.

The near-infrared ray sensor is a sensor for detecting infrared rays in an area near visible light, capable of detecting an infrared ray in a wavelength range about 700 μm to 1600 μm.

Light can be irradiated to the meat product 30 through the sensor 110. A part of the light irradiated to the meat product 30 is absorbed into the meat product 30, and remaining light is scattered and reflected at a surface of the meat product 30. Accordingly, the sensor 110 integrates the scattered and reflected light on the surface of the meat product 30, and measures the light intensity of the integrated light by wavelengths.

When the light intensity of the integrated light is measured by wavelengths, a controller 120 to be described later obtains state information on the meat product 30 based on the light intensity information of the light intensity of the measured light wavelength. Here, the state information may include at least one of a type of meat product, a degree of ripening, and a content of nutrition components.

Meanwhile, the sensor 110 provided on one side of the first area 20 is movable in left and right directions. When a plurality of different foods are stored in the first area 20, the sensor 110 moves left and right to integrate scattered and reflected light from each of the plurality of foods stored in the first area 20, and may measure the light intensity by wavelengths of the integrated light.

As described above, when the light intensity of each of the plurality of foods is measured according to the wavelength of light, the controller 120 to be described later may obtain state information of each of the plurality of foods based on the light intensity information by the measured light wavelength.

In addition, when a plurality of foods (e.g., apples) which are the same to each other are stored in the first area 20, the sensor 110 moves left and right, integrate scattered and reflected light from each food, and measure light intensity by wavelengths of integrated light.

As described above, when the light intensity for each of the plurality of the same foods is measured, the controller 120 may acquire one light intensity information from the light intensity of the respective light wavelengths measured from the same plurality of foods.

For example, the controller 120 may calculate an average value of light intensities measured from each of the plurality of foods, and obtain light intensity information based on the calculated average values of the light intensities. Then, the controller 120 can acquire state information on the same plurality of foods based on the obtained light intensity information.

According to one embodiment, the electronic device 100 may obtain state information on the meat product 30 using a plurality of pre-stored food-specific state change models. Specifically, the electronic device 100 obtains a state change model for the meat product 30 among a plurality of pre-stored state change models for each food based on the light intensity information of the meat product 30. Then, the electronic device 100 applies the state intensity change model to the meat product 30 based on the light intensity of the specific wavelength area among the light intensities of the meat product 30, and obtain state information of the meat product 30.

According to yet another exemplary embodiment, the electronic device 100 may receive state information about the meat product 30 from an external server 200. Specifically, the electronic device 100 transmits light intensity information of each wavelength measured from the meat product 30 to the external server 200 through the sensor 110. Accordingly, the external server 200 obtains the state change model for the meat product 30 among the plurality of pre-stored food-specific state change models based on the light intensity information of the meat product 30 received from the electronic device 100. Then, the external server 200 may apply the light intensity of the specific wavelength area of the light intensity of the meat product 30 to the state change model for the meat product 30, and send state information for the obtained meat product 30 to the electronic device 100.

When the state information on the meat product 30 is obtained through the various embodiments as described above, the electronic device 100 determines the state of the meat product 30 based on the obtained state information on the meat product 30 and controls at least one of temperature and humidity of the first area 20 in which the meat product 30 is stored based on the determined result.

The electronic device 100 displays a guide UI for state information of the meat product 30 through a display screen 10 attached on a front surface of a door for opening and closing a storage room which stores foods.

For example, based on the state information of the meat product 30, if it is determined that freshness of the meat product 30 is 'medium degree', the guide UI for the meat product 30 indicating "storage available for three days" can be provided according to the determined freshness.

Accordingly, the user can not only recognize that the meat product 30 is stored in the first area 20 through the guide UI displayed on the display screen 10 attached to the front side of the door of the electronic device 100 but also grasp the freshness state of the meat product 30. Thus, the user can take the meat product 30 before the state of the meat product 30 is altered.

Hereinbelow, each feature of the electronic device 100 will be described in a greater detail.

Figure 2:
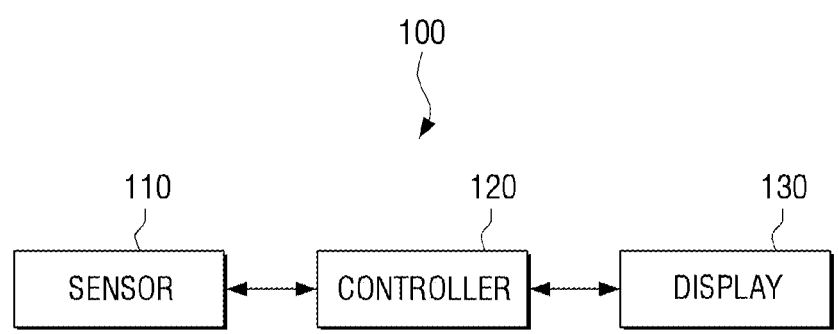
FIG. 2 is a block diagram of an electronic device according to an exemplary embodiment.

FIG. 2 is a block diagram of an electronic device according to an exemplary embodiment.

As illustrated in FIG. 2, the electronic device 100 may include the sensor 110, the controller 120, and the display 130.

The sensor 110 measures the light intensity of the light reflected by the food by using the infrared sensor. Here, the infrared sensor may be a near infrared sensor (NIR). The near-infrared ray sensor is a sensor for detecting infrared rays in an area close to visible light, and detects infrared rays in a wavelength range of about 700 to 1600 μm.

Figure 3:
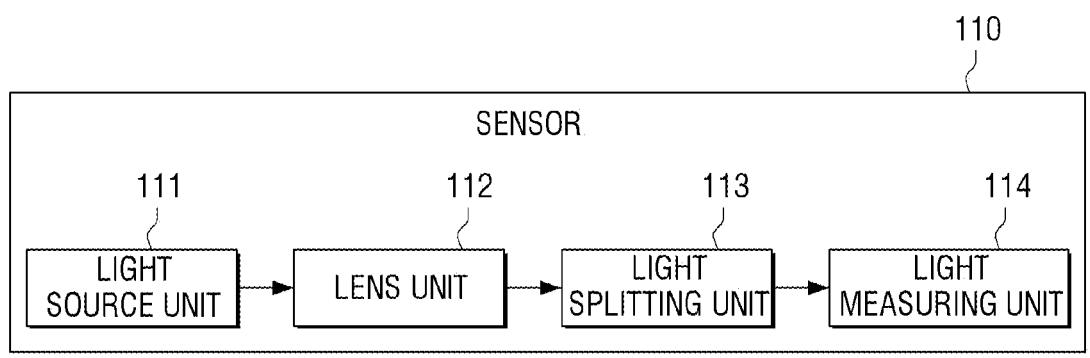
FIG. 3 is a detailed block diagram of a sensor according to an exemplary embodiment.

The sensor 110 may be configured as FIG. 3.

FIG. 3 is a detailed block diagram of a sensor according to an exemplary embodiment.

As illustrated in FIG. 3, the sensor 110 includes a light source unit 111, a lens unit 112, a light splitting unit 113, and a light measuring unit 114.

The light source unit 110 irradiates near-infrared light with food, and the lens unit 112 integrates light. Accordingly, a part of the light irradiated with food is absorbed into food by the chemical bonding structure of carbon-hydrogen (CH) and oxygen-hydrogen (OH) of the organic molecules constituting the food and the rest of light is scattered and reflected on a surface of the food.

Therefore, the lens unit 112 integrates the light scattered and reflected on the surface of the food irradiated with the food, and the light splitting unit 113 separates the light integrated through the lens unit 112 into the respective wavelength bands, and generates spectrum. The light measuring unit 114 analyzes the light spectrum separated by wavelength bands and measures the light intensity of the light scattered and reflected on the surface of the food.

When the light intensity by wavelengths of light, which is irradiated and reflected onto the food, is measured through the sensor 110, the controller 120 may determine a status of the food based on the light intensity by wavelengths of light of the measured food.

Specifically, the controller 120 obtains state information on the food based on the light intensity information measured by the sensor 110. Here, the state information may include at least one of the type of the food, the degree of ripening, and the content of the nutrient.

The controller 120, based on at least one of obtained status information and food usage plan information which is input by a user, adjusts at least one of temperature and humidity of an area where the corresponding food is disposed.

According to an exemplary embodiment, the controller 120 may obtain status information of the food (hereinafter, the first food) of which light intensity is measured based on a state change model of a plurality of foods prestored in the storage 140.

Specifically, when the light intensity of each light wavelength is measured by the sensor 110, the controller 120 obtains light intensity information of the first food based on the measured light intensity. The controller 120 may acquire the state change model of the first food among the plurality of food state change models pre-stored in the storage 140 based on the light intensity information of the first food.

Here, the plurality of pre-stored state change models for each food item may be used to measure the light intensity of each of the foods by time, by accumulating the measured light intensities.

An operation of generating a state change model of the food will be described in a greater detail below.

Meanwhile, when the state change model of the first food is obtained, the controller 120 applies the light intensity of the specific section among the light intensities of the light wavelength measured from the first food to the state change model, and the storage state such as freshness or ripening of the first food can be determined based on the acquired state information.

Specifically, the controller 120 applies the light intensity of the first specific period of the light intensity of each light wavelength measured from the first food to the state change model, and obtains a sample value related to light intensity of the first specific period from the state change model. Then, the controller 120 may determine the storage state of the first food based on the set state information including the sample value.

For example, the section including the sample value acquired in relation to the light intensity of the first specific section may be set as a section of which freshness state is good. When the state information of the first food is obtained, the controller 120 may maintain the temperature of the area where the first food is arranged based on the acquired state information or estimate a date until the food can be stored and provide the estimated date on the display screen 10.

According to still another exemplary embodiment, the controller 120 may acquire state information of the first food from the external server 200. The external server 200 may be a server for analyzing and managing a state change of each food based on the state change models generated by foods.

Specifically, when the light intensity information is obtained from the light intensity of each wavelength measured from the first food, the controller 120 controls the communicator 150 to transmit the obtained light intensity information to the external server 200. Accordingly, the communicator 150 transmits the light intensity information of the first food to the external server 200, and the external server 200 obtains the state change model of the first food, from among the plurality of prestored state change models, based on the light intensity information received from the electronic device 100.

The external server 200, based on light intensity of the first food received from the electronic device 100, applies light intensity of a specific wavelength section from among light intensities of the first food and determines a state of the first food. Then, the external server 200 transmits the determined state information of the first food to the electronic device 100, and the controller 120 may obtain the state information of the first food received from the external server 200 through the communicator 150.

When the status information of the first food is obtained through the various embodiments, the controller 120 determines whether or not the status information of the first food is obtained based on at least one of the acquired status information of the first food and the usage plan information input in relation to the first food, thereby adjusting at least one of temperature and humidity of the area where the first food is disposed.

According to one embodiment, when the state of the first food is determined to be low, based on the acquired state information, the controller 120 controls at least one of temperature and humidity of an area where the first food is disposed so that the first food can be stored for a long period of time.

For example, the first food may be stored in the first area of the refrigerating chamber, and the temperature of the first area in which the first food is stored may be set at 2° C. As such, when the temperature of the first area of the refrigerating chamber is set and the state of the first food stored in the first area is determined to be low, the controller 120 may control temperature of the first area to from 2° C. to 1° C. so that the first food can be stored for a long time. Accordingly, the cold air supply unit 160, which will be described later, of the electronic device 100 may supply cold air to the first area according to a control command of the controller 120 so that the temperature of the first area in which the first food is stored is maintained at 2° C. to −1° C.

Accordingly, the first food can be stored in the first area in a state where it can be consumed for a longer period of time.

According to another embodiment, when the state of the first food is determined to be low state and the first food is stored for a long period of time based on the usage plan information input by the user, it is possible to control at least one of temperature and humidity of the first area where the first food is stored so that the first food can be stored for a long time.

Here, the usage plan information may be information on an expected date when the user may eat the first food.

For example, the user can input usage plan information for consuming the first food one day after the storage day. If it is determined that the state of the first food is bad, the controller 120 may determine that the first food can be stored for two days based on the predetermined storable information.

In this case, if it is determined that the first food is not consumed on the date corresponding to the usage plan information input from the user, the controller 120 may adjust at least one of the temperature and the humidity of the first area where the first food is stored so that the first food can be stored for a long time.

For example, the first food may be stored in the first area of the refrigerating chamber, and the temperature of the first area where the first food is stored may be set at 2° C. If it is determined that the first food is not consumed on the date corresponding to the usage plan information input from the user, the controller 120 sets the temperature of the first area from 2° C. to −1° C. so that the first food can be stored in the first area for a long time.

Here, the temperature adjustment to −1° C. may be a temperature value which is set to be appropriate for long-term storage.

As a still another example, the user may input usage plan information for consuming the first food 5 days after the storage day. If it is determined that the state of the first food is a bad state, the controller 120 may determine that the first food can be stored for two days based on the predetermined storable information. In this case, the controller 120 determines whether or not the scheduled consumption date of the first food is earlier than the storable date based on the state information and the usage plan information of the first food.

As a result of determination, if the scheduled consumption date is later than the storable date, the controller 120 may adjust at least one of the temperature and humidity of the area where the first food is positioned so that the first food can be stored for a long time.

For example, the first food may be stored in the first area of the refrigerating chamber, and the temperature of the first area where the first food is stored may be set to 2° C. In the meantime, if it is determined that the scheduled consumption date of the first food stored in the first area is later than the storable date, the controller 120 may adjust temperature of the first area from predetermined 2° C. to 0° C. so that the first food can be consumed on the scheduled consumption date set by the user.

Accordingly, the cool air supply unit 160, which will be described later, of the electronic device 100 may supply cool air to the first area so that temperature of the first area in which the first food is stored can be maintained from 2° C. to 0° C., according to a control command of the controller 120.

Here, the temperature control to 0° C. may be a temperature value that is set in consideration of the scheduled consumption date and the storable date of the first food stored in the first area. That is, the controller 120 can adjust the temperature differently according to the degree of difference between the scheduled consumption date of the first food stored in the first area and the storable day, according to predetermined conditions.

However, the present disclosure is not limited thereto, and the controller 120, if the scheduled consumption date of the first food stored in the first area is later than the storable date, may adjust temperature to the preset temperature.

In the meantime, if it is determined that the scheduled consumption date is not later than the storable date, the controller 120 may maintain temperature of the first area in which the first food is stored as temperature of the first area.

According to still another exemplary embodiment, the controller 120, if the use plan information for long-term storage is input, may adjust at least one of temperature and humidity of the first area in which the first food is stored so that the first information can be stored for a long time based on the state information of the first food.

For example, the first food may be stored in the first area of the refrigerating chamber, and the temperature of the first area where the first food is stored may be set at 2° C. If the state of the first food stored in the first area is determined as high state (high freshness), the controller 120 may control the temperature of the first area in which the first food is stored to be from 2° C. to 1° C.

When the state of the first food stored in the first area is a medium class (medium freshness), the temperature of the first area where the first food is stored is can be set from 2° C. to 0° C.

When the state of the first food stored in the first area is a low class (low freshness), the temperature of the first area where the first food is stored is can be set from 2° C. to −1° C.

According to still another exemplary embodiment, the controller 120, when the usage plan information for rapid ripening is input, may adjust temperature and humidity of the first area where the first food is stored so that the first food can be ripen within a period corresponding to the usage plan information for rapid ripening based on the state information of the first food.

For example, the first food can be meat and the state of the first food which is meat can be classified into high grade (high freshness). The temperature of the first area where the first food is stored can be set from to 0° C.

In this case, the controller 120 may adjust the temperature of the first area in which the first food is stored from 0° C. to a temperature corresponding to the predetermined condition, according to the usage plan information for rapid ripening. Here, the temperature (0° C.) of the first area where the first food is stored may be a general temperature set according to a manual.

According to an exemplary embodiment, the ripening period of the first food (meat) may be set according to a state of the first food and temperature of the first area wherein the first food is stored.

For example, if the temperature of the first area where the first food as meat is stored is set at 0° C. and the state of the first food is the high class (high freshness), the ripening period of the first food may be set to seven days from the date of storage in the first area.

When the temperature of the first area where the first food is stored is set to 0° C., and the state of the first food is a medium class (medium freshness), the ripening period of the first food may be set to three days from the date of storage in the first area.

When temperature of the first area where the first food which is meat is stored is set to 0° C., and the state of the first food which is meat is low grade (low freshness), the ripening period of the first food may be set to one day from the storage date of the food in the first area.

When temperature of the area where the first food is stored is raised by 1° C. from 0° C., the date of ripening may be set to one day earlier according to the state of the first food which is meat.

According to this example, when the user sets the scheduled ripening date of the first food as five days after the first food is stored in the first area, and it is determined that the state of the first food which is set at the temperature of 0° C. is in a high class, the controller 120 may set the temperature of the first area where the first food is stored to be increased from 0° C. to 2° C.

Accordingly, the cold air supplier 160 to be described later of the electronic device 100 can adjust cold air supply of the first area so that the temperature in the first area where the first food is stored increases from 0° C. to 2° C.

In the meantime, the controller 120 controls the display 130 to display a guide UI for state information obtained in association with the first food on the screen. Accordingly, the display 130 displays the guide UI for the first food on the screen. Here, the guide UI may include a first UI element for providing a state of the first food and a second UI element for providing recipe information for the first food.

However, the present disclosure is not limited thereto, and the guide UI may further include an UI element for inputting usage plan information for the aforementioned first food.

According to the guide UI which is displayed through the display 130, a user may confirm a state of the first food, recipe information which can be used for the first food, and a kind of the food stored in the first area and so on.

Figure 4:
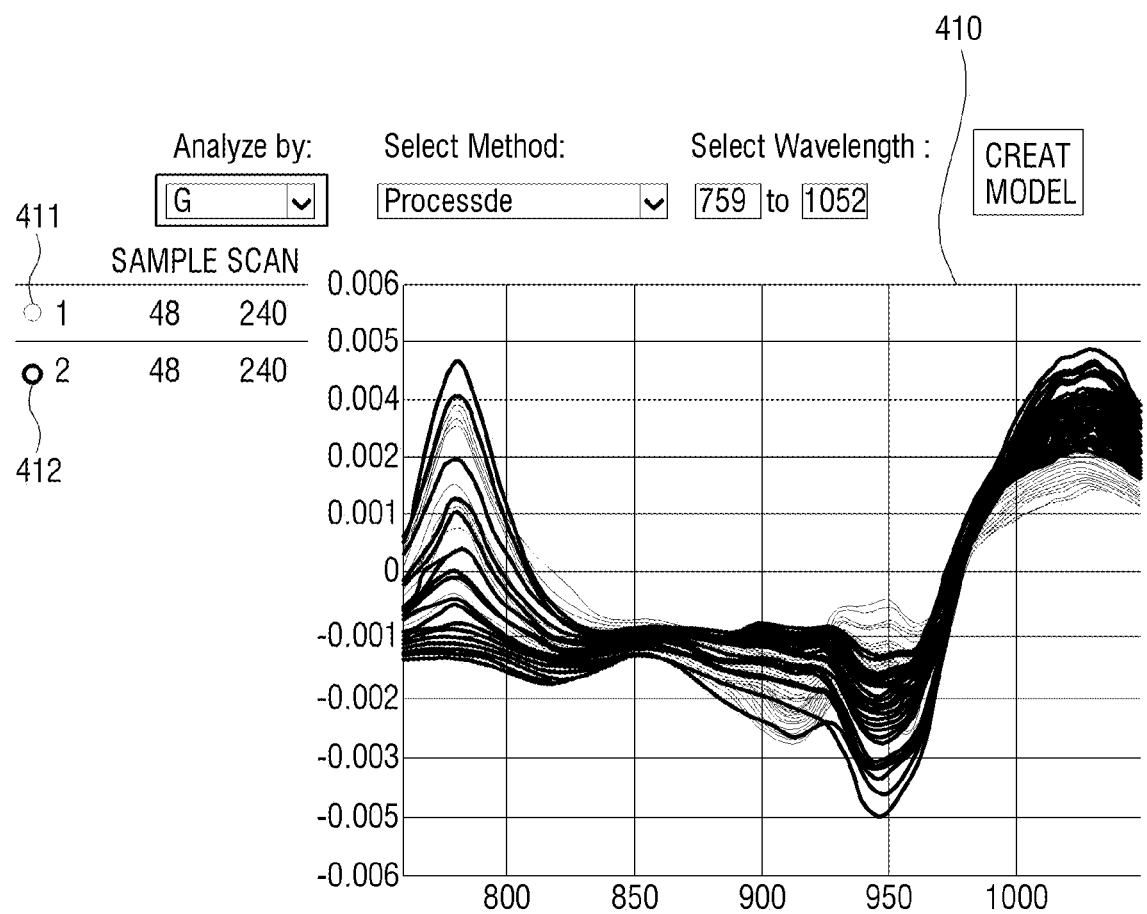
FIG. 4 is an exemplary diagram to generate a food state change model according to an exemplary embodiment.

FIG. 4 is an exemplary diagram to generate a food state change model according to an exemplary embodiment.

The state change model can be generated by irradiating the food with light using infrared sensor on a time unit basis for each food and accumulating the light intensity measured from the wavelength of the reflected light.

For example, as shown in FIG. 4, in the case of the first food, which is meat, the first food classified by grade is irradiated with light through an infrared sensor in units of time, and the wavelength of the reflected light is measured. The state change model 410 for the first food can be generated by accumulating the light intensity measured for each wavelength of light.

Specifically, in the case of the first food 411 classified into the first grade, as shown in the figure, the first food 411 is irradiated with light for 48 times in a predetermined time unit, and the wavelength of light scattered and reflected on the surface of the food 411 is measured to accumulate the light intensity measured for each wavelength of light.

Similarly, in the case of the second food 412 classified into the second grade, light is irradiated to the second food 412 for 48 times in a predetermined time unit as shown in the figure, and the intensity of light measured by wavelengths of light is accumulated by measuring the wavelength of the light scattered and reflected at the surface of the second food 412.

Through this experiment, a state change model 410 for the first and second foods 411 and 412 classified into the first and second grades can be generated.

Hereinafter, the operation of providing information according to the state of the first food in the electronic device 100 will be described in detail.

Figure 5:
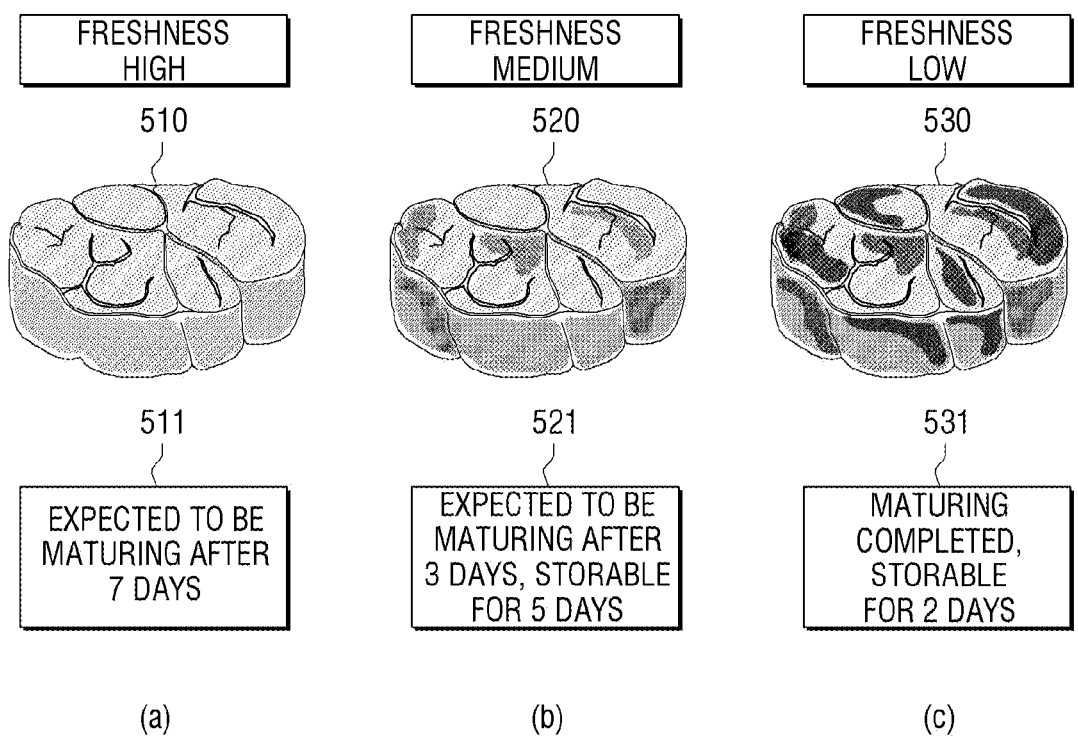
FIG. 5 is a first exemplary diagram for providing a guide UI for food stored in an electronic device according to an exemplary embodiment.

FIG. 5 is a first exemplary diagram for providing a guide UI for food stored in an electronic device according to an exemplary embodiment.

As shown in FIG. 5A, the meat product may be stored in the first area of the electronic device 100, and the freshness of the meat product 510 stored in the first area may be determined as high. The electronic device 100 may input usage plan information for ripening the meat product 510 from the user. In addition, the temperature of the first area where the meat product 510 is stored may be set to a predetermined proper temperature (for example, 0° C.).

In this case, the electronic device 100 may predict the scheduled date of ripening of the meat product 510 based on the freshness state of the meat product 510, usage plan information of the meat product 510, and the temperature of the first area where the meat product 510 is stored.

Thereafter, the electronic device 100 displays a guide UI 511 for the meat product 510, which is 'expected to be maturing after 7 days', based on the predicted result regarding the ripening of the meat product 510 on the display screen attached to the front surface of the door that opens and closes the storage room for storing the food.

As shown in FIG. 5 (b), freshness of the meat product 520 stored in the first area of the electronic device 100 can be determined as medium. In the electronic device 100, usage plan information for ripening the meat product 520 may be input from the user. In addition, the temperature of the first area where the meat product 520 is stored may be set to a predetermined proper temperature (for example, 0° C.).

In this case, the electronic device 100 may predict the estimated ripening date of the meat product 520 based on a freshness state, usage plan information of the meat product 520 or temperature of the first area where the meat product 520 is stored.

In addition, the electronic device 100 can estimate the storable date of the meat product 520 considering the freshness state of the meat product 520 and the temperature set in the first area where the meat product 520 is stored.

For example, in consideration of the freshness state of the meat product 520 and the appropriate temperature of the area in which the meat product 520 is stored, the electronic device 100 may store a table mapped with a storable date of the meat product 520 by freshness states in the storage 140.

The [Table 1] mapped with the storable date by freshness state of the meat product 520 can be generated as shown below.

TABLE 1

| Meat product state | Temperature | Estimated storage date |
| --- | --- | --- |
| High freshness (上) | Proper temperature | 7 days |
| Medium freshness (中) | Proper temperature | 5 days |
| Low freshness (下) | Proper temperature | 2 days |

Accordingly, the electronic device 100 can determine the storable date of the meat product 520 with reference to the above table [Table 1].

As described above, when the ripening date and the storable date of the meat product 520 are predicted, the electronic device 100 determines that the meat product 520 is expected to be aged after 3 days and can be stored for 5 days, and displays the guide UI 521 for the meat food 520 on the display screen attached to the front surface of the door that opens and closes the storage room for storing food.

As illustrated in FIG. 5(*c*), the meat food 530 stored in the first area of the electronic device 100 can be ripen for a time which corresponds to the usage plan information for ripening the meat food 530 As described above, the freshness of the ripen meat food 530 can be lower.

In this case, the electronic device 100 can estimate the storable date of the meat product 510 based on the freshness state of the meat product 530 and the temperature set in the first area where the meat product 53 is stored.

As described above, when the meat product 530 is completely ripened and the storable date is predicted, the electronic device 100 determines that the meat product 530 has been completely aged based on the predicted result, and can display a guide UI 530 indicating the meat product 530 indicating 'ripening completed' and 'storable for two days' on a display screen attached to the front of a door that opens and closes a storage room for storing foods.

Figure 6:
FIG. 6 is a second exemplary diagram for providing a guide UI for food stored in an electronic device according to yet another exemplary embodiment.

FIG. 6 is a second exemplary diagram for providing a guide UI for food stored in an electronic device according to yet another exemplary embodiment.

As shown in FIG. 6, the electronic device 100 can mature the meat food stored in the first area of the electronic device 100 based on the ripening-related usage plan information input from the user.

When the ripening is completed based on the ripening-related usage plan information, the electronic device 100 not only provides a guide UI for guiding the completion of ripening, as described in FIG. 5, but also, as in FIG. 6, the electronic device 100 may display a guide UI 610 including cooking-related recipe information using ripened meat products on a display screen attached to the front of the door.

Specifically, the electronic device 100 may acquire recipe information related to cooking using meat product among the recipe information for each food stored in the storage 140 or acquire recipe information related to the recipe information using meat product or ripened meat to receive and acquire cooking-related recipe information using the food.

Likewise, when the meat product recipe information is obtained, the electronic device 100 may display the guide UI 610 which includes recipe information obtained in association with the meat product on the display screen attached to the front surface of the door for opening and closing the storage room for storing the food.

Figure 7:
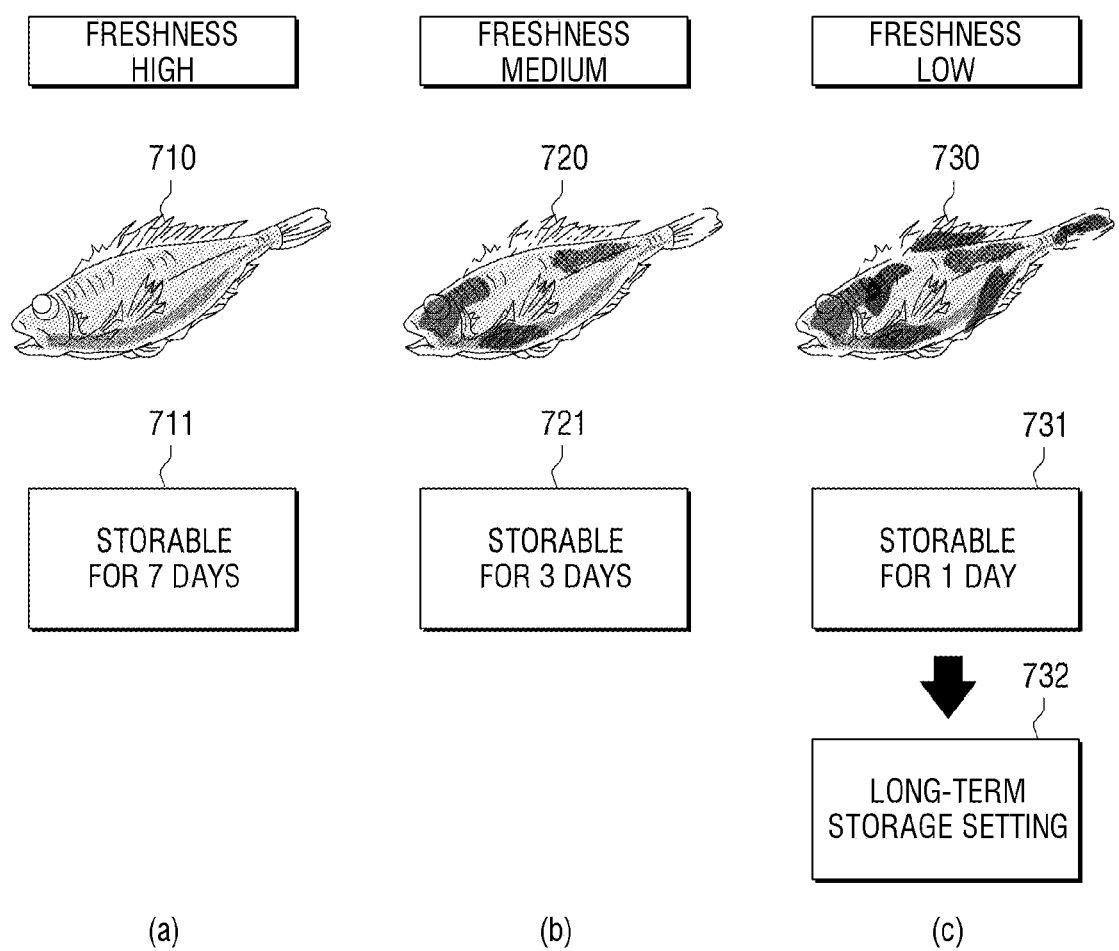
FIG. 7 is a third exemplary diagram for providing a guide UI for food stored in an electronic device according to yet another exemplary embodiment.

FIG. 7 is a third exemplary diagram for providing a guide UI for food stored in an electronic device according to yet another exemplary embodiment.

As shown in FIG. 7A, fish food 710 can be stored in the first area of the electronic device 100, and the freshness of the fish food 710 stored in the first area can be determined to be high. The temperature of the first area where the fish food 710 is stored may be set to a predetermined proper temperature (for example, 0° C.).

In this case, the electronic device 100 can predict the storable date of the fish food 710 by referring to a table stored in the storage 140, which will be described later.

Specifically, the storage 140 may store a table in which the storable date of the fish food 710 is mapped according to the freshness state in consideration of the freshness state of the fish food 710 and the appropriate temperature of the area where the fish food is stored.

Accordingly, the electronic device 100 refers to the table stored in the storage 140 to determine the storable date of the fish food 710 whose freshness is determined to be higher. Then, based on the determination result, the electronic device 100 displays the guide UI 711 indicating 'storable for seven days' for the fish food 710 on the display screen attached to the front of the door for opening and closing the storage room for storing food.

As shown in FIG. 7 (*b*), the electronic device 100 can determine the freshness of the fish food 720 stored in the first area as medium. The temperature of the first area where the fish food 720 is stored may be set to a predetermined proper temperature (for example, 0° C.).

In this case, the electronic device 100 refers to the pre-stored table to determine the storable date of the fish food 720 whose freshness is determined to be medium. Thereafter, the electronic device 100 displays the guide UI 721 for the fish food 720, which can be stored for 3 days, on the display screen attached to the front of the door for opening and closing the storage room for storing the food.

Meanwhile, as shown in FIG. 7C, the freshness of the fish food 730 stored in the first area can be determined to be low. The temperature of the first area where the fish food 730 is stored may be set to a predetermined proper temperature (for example, 0° C.).

In this case, the electronic device 100 refers to the pre-stored table to determine the storable date of the fish food 730 whose freshness is determined to be low. Thereafter, the electronic device 100 may display a guide UI 731 indicating 'storable for one day' for the fish food 730 on the display screen attached to the front of the door for opening and closing the storage room for storing food.

In the meantime, the electronic device 100 determines whether the fish food 730 whose freshness is lower is stored in the first area for an extended period of time. Specifically, the electronic device 100 can determine whether the fish food 730 is being stored in the first area for a long period of time based on the predictable storable date in relation to the fish food 730 whose freshness is low.

If it is determined that the fish food 730 is being stored in the first area for a long period of time, the electronic device 100 may adjust the temperature of the first area where the fish food 730 is stored at an appropriate temperature (for example, 0° C.) to be set to be the temperature (for example, −2° C.) suitable for long term storage.

As described above, when it is determined that the fish food 730 having the low freshness is stored in the first area for a long period of time, the electronic device 100 adjusts the temperature of the first area stored in the fish food 730 to be lower. Accordingly, the fish food 730 stored in the first area can be stored in the first area for an extended period of time while maintaining the current freshness state.

However, the present disclosure is not limited thereto, and the user can check the guide UI 731 of 'storable for one day' displayed on the screen of the door of the electronic device 100 and enter a user command for long-term storage.

When the user's usage plan information is input in connection with such a long-term storage, the electronic device 100 may adjust the temperature (for example, 0° C.) of the first area where the fish product 730 is stored to the temperature (for example, −2° C.) which is set to be suitable for long-term storage.

Meanwhile, when the electronic device 100 sets the long-term storage of the fish food 730 stored in the first area, the electronic device 100 may display the guide UI 732 indicating 'long-term storage setting' for the fish food 730 on the display screen attached to the front surface of the door that opens and closes the storage room for storing the food.

Figure 8:
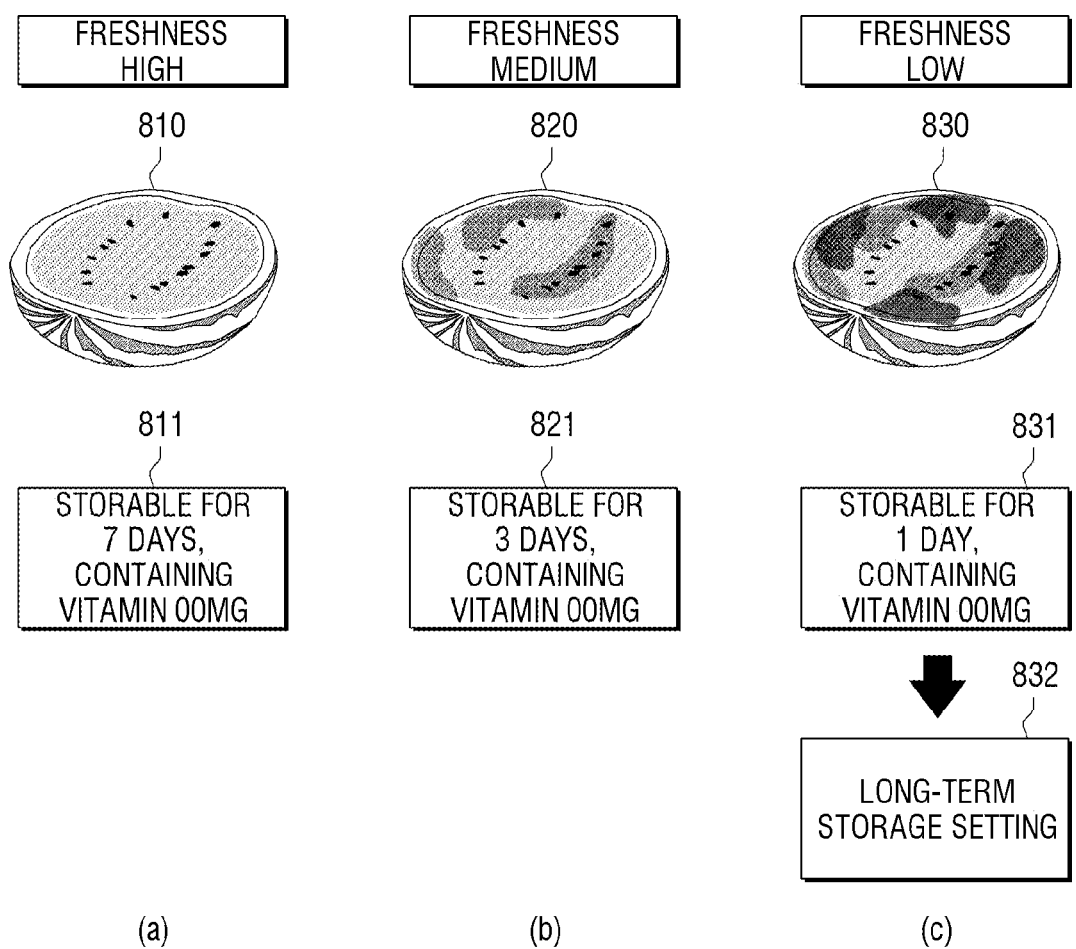
FIG. 8 is a third exemplary diagram for providing a guide UI for food stored in an electronic device according to yet another exemplary embodiment according to an exemplary embodiment.

FIG. 8 is a third exemplary diagram for providing a guide UI for food stored in an electronic device according to yet another exemplary embodiment according to an exemplary embodiment.

As shown in FIG. 8 (a), fruit food 810 can be stored in the first area of the electronic device 100. The electronic device 100 may obtain the state information of the fruit food 810 based on the light intensity of the light of the fruit food 810 measured through the sensor 110.

Here, the obtained state information may include at least one of the type of the fruit food 810, freshness state, and content information of the nutrients.

When the state information is obtained, the electronic device 100 determines that the fruit food 810 stored in the first area is watermelon based on the acquired state information, and that the freshness is higher degree. The temperature of the first area where the fruit food 810 is stored may be set to a predetermined proper temperature (for example, 0° C.).

In this case, the electronic device 100 may predict a storable date of the fruit food 810 with reference to a table prestored in the storage 140 to be described later.

More specifically, the storage 140 may store a table mapped with the storable date by the freshness state of the fruit food 810 in accordance with the freshness state of the fruit food 810 and the appropriate temperature of the area where the fruit food 810 is stored.

Accordingly, the electronic device 100 refers to the table stored in the storage 140 to determine the storable date of the fruit food 810 whose freshness is determined to be high.

Further, the electronic device 100 can predict the vitamin content contained in the fruit food 810 based on the information on the content of the nutrition ingredient contained in the estimated state information.

Thus, if the storable date and the vitamin content for the fruit food 810 are predicted, the electronic device 100 may display the guide UI 811 'storable for seven days' and 'containing vitamin by 00 mg' regarding the fruit food 810 based on the predicted result on the display screen attached to the door which opens and closes a storage room for storing the food.

As illustrated in FIG. 8 (b), the electronic device 100 may determine the freshness of the fruit food 820 stored in the first area based on the state information of the fruit food 820 to be medium. The temperature of the first area where the fruit food 820 is stored may be set to a predetermined proper temperature (for example, 0° C.).

In this case, the electronic device 100 refers to the pre-stored table to determine the storable date of the fruit food 820 whose freshness is determined to be medium.

In addition, the electronic device 100 can predict the vitamin content contained in the fruit food 820 based on the information on the content of the nutrition ingredient contained in the state information of the fruit food 820. Here, it is preferable that the vitamin content contained in the freshness-medium fruit food 820 is lower than the vitamin content contained in the fruit food 810 whose freshness is high.

Then, based on the predicted result, the electronic device 100 displays a guide UI 821 indicating 'storable for three days' and 'containing vitamin 00 mg' based on the predicted result on a display screen attached to a front side of the door which opens and closes the storage room storing the food.

On the other hand, as shown in FIG. 8 (c), the freshness of the fruit food 830 stored in the first area can be judged to be low. The temperature of the first area where the fruit food 830 is stored may be set to a predetermined proper temperature (for example, 0° C.).

In this case, the electronic device 100 refers to the pre-stored table to determine the storable date of the fruit food 830 whose freshness is determined to be low.

In addition, the electronic device 100 can predict the vitamin content contained in the fruit food 820 based on the content information on the nutritional content included in the state information of the fruit food 830. Here, it is preferable that the vitamin content contained in the fruit food 830 whose freshness is low is smaller than the vitamin content contained in the fruit food 820 whose freshness is medium.

Thereafter, based on the predicted result, the electronic device 100 may display a guide UI 831 for the fruit food 830 indicating 'storable for one day' and 'containing vitamin 00 mg' on the display screen attached to the front of the door which opens and closes a storage room for storing the food.

In the meantime, the electronic device 100 determines whether the fruit food 830 whose freshness is low is stored in the first area for an extended period of time. Specifically, the electronic device 100 can determine whether the fruit food 830 is being stored in the first area for a long period of time based on the predictable storage date in relation to the fruit food 830 whose freshness is low.

As a result of the determination, if it is determined that the fruit food 830 is stored in the first area for a long period of time, the electronic device 100 adjusts the temperature of the first area in which the fruit food 830 is stored from an appropriate temperature (for example, 0° C.) to a set temperature (e.g., −1° C.).

As described above, when the electronic device 100 determines that the fruit food 830 whose freshness state is low is stored in the first area for an extended period of time, the electronic device adjusts the temperature of the first area stored in the fruit food 830 to be lower. Accordingly, the fruit food 830 stored in the first area can be stored in the first area for a long period of time while maintaining the current freshness state.

However, the present disclosure is not limited thereto, and the user may check the guide UI 831 of 'storable for one day' displayed on the screen of the door of the electronic device 100, and enter a user command for long-term storage.

When the user's usage plan information is input in association with the long-term storage, the electronic device 100 may adjust the temperature of the first area in which the fruit food 830 is stored from an appropriate temperature (for example, 0° C.) to a set temperature (e.g., −1° C.) for long term storage.

On the other hand, when the long-term storage of the fruit food 830 stored in the first area is set, the electronic device 100 may display the guide UI 832 for the fruit food 830 indicating 'long-term storage setting' on the display screen attached to the front surface of the door that opens and closes the storage room for storing the food.

Hereinafter, the detailed configuration of the above-described electronic device 100 will be described in detail.

Figure 9:
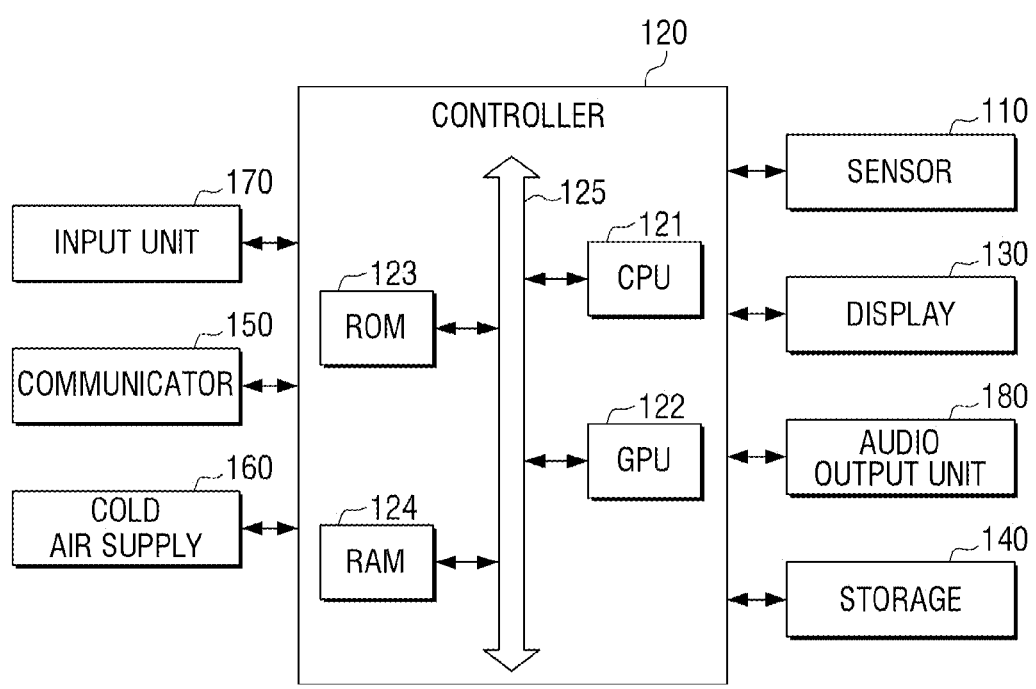
FIG. 9 is a detailed block diagram of an electronic device according to an exemplary embodiment.

FIG. 9 is a detailed block diagram of an electronic device according to an exemplary embodiment.

The electronic device 100 may be a smart refrigerator that stores various foods such as meat, fruit, fish, and the like. As illustrated in FIG. 9, the electronic device 100 includes a storage 140, a communicator 150, a cool air supply unit 160, an input unit 170, and an audio output unit 180 in addition to the sensor 110, the controller 120, and the display 130.

As described above, the sensor 110 irradiates light to foods stored in an area in the electronic device 100, and measures light intensity of each food by wavelengths from scattered and reflected light.

In addition, the sensor 110 may further include a temperature sensor module for measuring the temperature of each area of the electronic device 100.

The controller 120 controls the operation of each component of the electronic device 100 as a whole. In particular, the controller 120 controls the temperature of the food stored in the sensor 110 based on the state information of the food obtained based on the light intensity of each light wavelength with respect to the food.

The display 130 displays a guide UI including at least one of the food condition and the recipe information related to the food on the screen. The display 130 may be a liquid crystal display (LCD), an organic light emitting diode (OLED), or the like. As described above, the display 130 may include a door. The display 130 may be implemented as a touch screen capable of touch input by the user.

The storage 140 stores the state change model generated based on the light intensity of each light wavelength measured for each food item. In addition, the storage 140 may store a table in which at least one of the storable date information, the temperature and humidity setting information, and the recipe information is set based on state information of each food. In addition, the storage 140 may further store various operation programs for controlling the operation of the electronic device 100. Here, the operating program may be a program that is read and compiled in the storage 140 to operate each configuration of the user terminal device 100 when the electronic device 100 is turned on.

As described above, the communicator 150 includes an external server 200 for providing state information on food and a web server (not shown) for providing contents, a user terminal device such as a smart phone registered in advance, and performs data communication with the Internet of Things (IOT).

The communicator 150 may include a connector which includes at least one of a wireless communication module such as a short-range communication module and a wireless LAN module, and a wired communication module such as a high-definition multimedia interface (HDMI), a universal serial bus (USB), an IEEE (Institute of Electrical and Electronics Engineers) 1394, etc.

The short-range communication module is a configuration for wirelessly performing short-range communication between the electronic device 100 and a peripheral device (for example, a user terminal device, a destination Internet device). Such a short range communication module may include at least one of a BLUETOOTH module, an infrared data association module (IrDA), a Near Field Communication module (NFC) module, a WIFI module, and a Zigbee module.

A wireless communication module is a module that is connected to an external network and performs communication according to a wireless communication protocol such as IEEE. In addition, the wireless communication module further includes a mobile communication module for performing communication by accessing a mobile communication network according to various mobile communication standards such as 3rd Generation (3G), 3rd Generation Partnership Project (3GPP), Long Term Evolution (LTE).

As described above, the communicator 150 may be implemented by various short-range communication method and apply other communication technologies which are not mentioned in the specification if necessary.

Meanwhile, the connector is configured to provide interfaces with various source devices such as USB 2.0, USB 3.0, HDMI, and IEEE 1394. Such connector can receive state information on the food from the above-described external server 200 via the wired cable connected to the connector 153 or receive the content data transmitted from the web server (not shown). In addition, the connector can receive power from a power source via a wired cable that is physically connected to the connector.

The cold air supply unit 160 supplies cold air to the storage room for storing food in the electronic device 100 so that the predetermined temperature is maintained. In particular, when a different temperature is set for each area, the cool air supply unit 160 can supply cool air of different intensities to each area so that the cool air can be maintained at a set temperature for each area.

The input unit 170 receives a user command. The input unit 170 may include at least one of an operation unit, a touch input unit, a user input unit, and a microphone.

The operation unit may be implemented by a keypad having various function keys, numeric keys, special keys, character keys, etc. When the display 130 is implemented as a touch screen, the touch input unit can be implemented as a touch pad having a mutual layer structure with the display 130. In this case, the touch input unit can receive a touch command for various UI elements displayed through the display 130.

The user input unit receives an IR signal or an RF signal from a remote control device (not shown) that controls the electronic device 100, and the microphone receives a voice command of the user.

Finally, the audio output unit 180 outputs audio data related to the guide UI displayed through the display 130 in the form of an audible sound.

The controller 120 may include a CPU 121, a GPU 122, a ROM 123, and a RAM 124. The CPU 121, GPU 122, ROM 123, and RAM 124 may be interconnected via bus 125.

The CPU 121 accesses the storage 140 and performs booting using the OS stored in the storage 140. The CPU 121 also performs various operations using various programs, contents, data stored in the storage 140, and the like.

The GPU 122 generates a display screen including various objects such as icons, images, text, and the like. Specifically, the GPU 122 computes an attribute value such as a coordinate value, a shape, a size, and a color to be displayed by each object according to the layout of the screen based on the received control command, and generates display screens of various layouts including objects.

The ROM 123 stores a command set for booting the system and the like. When the turn-on command is input and power is supplied, the CPU 121 copies the OS stored in the storage 140 to the RAM 124 according to the command stored in the ROM 123, and executes the OS to boot the system. When the booting is completed, the CPU 121 copies various programs stored in the storage 140 to the RAM 124, executes the program copied to the RAM 124, and performs various operations.

The controller 120 may be implemented as a system-on-a-chip (SOC) or a system-on-chip (SoC) by being combined with the above-described features.

The operation of the controller 120 may be performed by a program stored in the storage 140. Here, the storage 140 may be implemented as at least one of a ROM 123, a RAM 124, or a memory card (such as an SD card or a memory stick) detachable/attachable to the electronic device 100, a non-volatile memory, a volatile memory, hard disk drive (HDD) or a solid state drive (SSD).

The detailed configuration of the electronic device 100 for managing food according to the present disclosure has been described in detail. Hereinafter, the control method of the electronic device 100 for managing the food according to the present disclosure will be described in detail.

Figure 10:
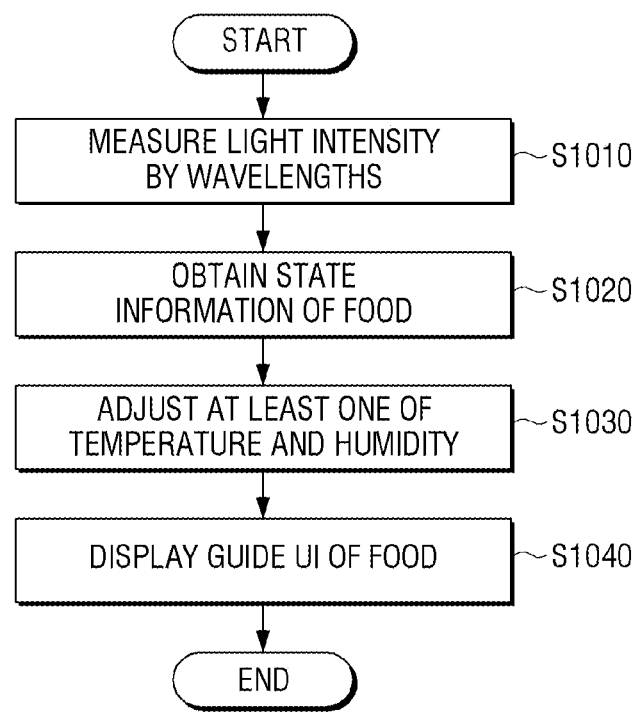
FIG. 10 is a flowchart of a control method of an electronic device for food management according to an exemplary embodiment.

FIG. 10 is a flowchart of a control method of an electronic device for food management according to an exemplary embodiment.

As shown in FIG. 10, the electronic device 100 irradiates food (hereinafter referred to as "first food") using an infrared sensor and measures light intensity of each wavelength of the reflected light (S 1010). Here, the infrared ray sensor is a near-infrared ray sensor that detects infrared rays in an area close to visible light, and can detect infrared rays in a wavelength range of about 700 to 1600 μm.

When the light intensity of the light of the first food is measured through the sensor, the electronic device 100 acquires state information on the first food based on the measured light intensity information (S 1020). Here, the state information may include at least one of a type for the first food, a ripening degree, and a nutritional content.

Specifically, the electronic device 100 can acquire status information on the first food through the following embodiment.

According to one embodiment, the electronic device 100 may obtain status information on the first food using a plurality of pre-stored food-specific state change models.

Specifically, the electronic device 100 acquires the state change model for the first food among the plurality of pre-stored state change models for each food based on the light intensity information of the first food. Then, the electronic device 100 can obtain the state information of the first food by applying the light intensity of the specific wavelength area of the optical intensity of the first food to the state change model of the first food.

According to another embodiment, the electronic device 100 may receive status information about the first food from the external server 200.

Specifically, the electronic device 100 transmits optical intensity information for each wavelength of the first food to the external server 200. Accordingly, the external server 200 acquires the state change model for the first food among the previously stored plurality of food-based state change models based on the light intensity information of the first food received from the electronic device 100. Then, the external server 200 may apply the light intensity of a specific wavelength section, from among the light intensities by wavelengths, to the obtained state change model of the first food to obtain the state information of the first food and transmit the state information of the first food to the electronic device 100.

Meanwhile, the electronic device 100 or the external server 200 can generate a food-specific state change model through the following embodiment.

Specifically, the electronic device 100 or the external server 200 irradiates the first food of the plurality of foods through the infrared sensor in units of time, and a part of the irradiated light is scattered on the surface of the first food and integrates scattered and reflected light. The electronic device 100 or the external server 200 may then accumulate the light intensity measured from the wavelength of the direct light to create a state change model that represents the temporal state change for the first food.

Meanwhile, when state information about the first food is obtained through the above-described various embodiments, the electronic device 100 determines the state of the first food based on at least one of the acquired state information on the first food and the usage plan information of the first food and adjusts at least one of the temperature and humidity of the area (hereinafter the first area) in which the first food is stored (S1030) based on the determined result.

Herein, the usage plan information may be information regarding a scheduled date for consuming the first food by a user.

After that, the electronic device 100 displays the guide UI for the first food on the screen attached to the front surface of the door for opening and closing the storage room for storing the food, based on the status information on the first food (S 1040).

Here, the guide UI for the first food may include at least one of a first UI element for providing the state of the first food and a second UI element for providing recipe information for the first food. However, the present disclosure is not limited thereto, and the guide UI may further include a UI element for inputting usage plan information for the first food.

The electronic device 100 may control at least one of the temperature and the humidity of the first area where the first food is stored through the following embodiments.

According to one embodiment, when the status of the first food is determined to be low based on status information on the acquired first food, the electronic device 100 may adjust at least one of temperature and humidity of the first of the first area where the first food is stored so that long-term storage is available.

According to yet another embodiment, the electronic device 100 determines that the state of the first food is low based on the acquired state information about the first food, and based on the usage plan information input from the user, the electronic device may determine whether or not the first food is stored in the first area for an extended period of time. If it is determined that the first food is stored in the first area for a long period of time, the electronic device 100 controls at least one of temperature and humidity of the first area so that the first food can be stored in the first area for a long period of time.

According to still another embodiment, when the usage plan information for long-term storage is input, the electronic device 100 may adjust, for the period corresponding to the usage plan information for long-term storage, based on the state information of the first food, at least one of temperature and humidity of the first area can be adjusted so that the food can be stored in the first area for an extended period of time.

According to another embodiment, when the usage plan information for rapid ripening is inputted, the electronic device 100 can adjust at least one of temperature and humidity of the first area where the first food is stored so that the food can be ripen in a period corresponding to the usage plan information for rapid ripening based on the state information of the first food.

According to these various embodiments, the electronic device 100 can adjust at least one of the temperature and the humidity of the first area where the first food is stored, depending on the state of the first food stored in the first area, store the first food for a long time or ripen as a state requested by the user.

In addition, the electronic device 100 according to the present disclosure includes a guide UI for providing a state of a first food stored in a first area through a screen attached to a front surface of a door for opening and closing a storage room for storing food. Accordingly, the user can check the state of the first food in real time through the guide UI displayed on the screen attached to the front surface of the door of the electronic device 100, and consume the food in various forms before the first food is spoiled.

The present disclosure has been described by centering on the preferred embodiments.

The non-transitory computer-recordable medium is not a medium configured to temporarily store data such as a register, a cache, or a memory but an apparatus-readable medium configured to semi-permanently store data. Specifically, the above-described various applications or programs may be stored in the non-transitory apparatus-readable medium such as a compact disc (CD), a digital versatile disc (DVD), a hard disc, a Blu-ray disc, a universal serial bus (USB), a memory card, or a read only memory (ROM), and provided therein.

The foregoing exemplary embodiments and advantages are merely exemplary and are not to be construed as limiting the inventive concepts. The exemplary embodiments may be readily applied to other types of device or apparatus. Also, the description of the exemplary embodiments is intended to be illustrative, and not to limit the scope of the inventive concepts, and many alternatives, modifications, and variations will be apparent to those skilled in the art. Although the present disclosure has been described with exemplary embodiments, various changes and modifications may be suggested to one skilled in the art. It is intended that the present disclosure encompass such changes and modifications as fall within the scope of the appended claims.

What is claimed is:

1. A control method of an electronic device for managing food included in the electronic device, the method comprising:
    irradiating light to an area where the food is disposed;
    measuring an intensity of light, which is reflected by the food, by wavelengths;
    obtaining state information of the food based on the measured intensity; and
    adjusting at least one of temperature and humidity of the area where the food is disposed based on the obtained state information and usage plan information,
    wherein the adjusting comprises:
        identifying a storable date of the food based on the obtained state information,
        identifying an expected date of consumption of the food based on the usage plan information,
        based on the storable date being earlier than the expected date, adjusting at least one of the temperature and the humidity of the area where the food is disposed,
        in response to identifying that a state of the food is a low grade based on the obtained state information, identifying a time period in which the food is stored in the electronic device, and
        in response to the time period being longer than a predetermined time period, adjusting the at least one of the temperature and the humidity to store the food for a long time period.

2. The method of claim 1, wherein the adjusting comprises, in response to the usage plan information for long-term storage being input, adjusting at least one of the temperature and the humidity so that the food is able to be stored for a long time based on the state information of the food.

3. The method of claim 1, wherein the adjusting comprises, in response to the usage plan information for rapid ripening being input, adjusting at least one of the temperature and the humidity so that the food is able to be ripened within a period corresponding to use plan information for the rapid ripening.

4. The method of claim 1, further comprising:
    displaying a guide UI for the food on a screen based on the obtained state information,
    wherein the guide UI comprises at least one of a first UI element for providing a food state and a second UI element for providing recipe information of the food.

5. The method of claim 1, wherein the obtaining comprises obtaining a state change model of the food from among a plurality of prestored state change models based on the measured intensity and obtaining food state information by applying light intensity of a specific wavelength from among light intensities by wavelengths of the food to the obtained state change model.

6. The method of claim 5, wherein the state change model is a model which is generated by accumulating light intensities measured from wavelength of light which is reflected by irradiating the food with light.

7. The method of claim 1, wherein the obtaining comprises transmitting the measured intensity to an external server and receiving the state information of the food determined based on the measured intensity from the external server.

8. The method of claim 1, wherein the state information comprises at least one of a type, ripening degree, and a content of nutrition of the food.

9. An electronic device for managing a food included in the electronic device, the electronic device comprising:
    a sensor configured to irradiate light to an area where food is disposed and measure an intensity of light, which is reflected by the food, by wavelengths; and
    a controller configured to:
        obtain state information of the food based on the measured intensity, and
        adjust at least one of temperature and humidity of the area where food is disposed based on the obtained state information and usage plan information,
        wherein during the adjusting the controller is further configured to:
            identify a storable date of the food based on the obtained state information,
            identify an expected date of consumption of the food based on usage plan information,
            based on the storable date being earlier than the expected date, adjust at least one of the temperature and the humidity of the area where the food is disposed,
            in response to identifying that a state of the food is a low grade based on the obtained state information, identify a time period in which the food is stored in the electronic device, and
            in response to the time period being longer than a predetermined time period, adjust the at least one of the temperature and the humidity to store the food for a long time period.

10. The electronic device of claim 9, wherein the electronic device, in response to the usage plan information for long-term storage being input, adjusts at least one of the temperature and the humidity so that the food is able to be stored for a long time based on the state information of the food.

11. The electronic device of claim 9, wherein the controller, in response to the usage plan information for rapid ripening being input, adjusts at least one of the temperature and the humidity so that the food is able to be ripened within a period corresponding to use plan information for the rapid ripening.

12. The electronic device of claim 9, further comprising:
a display,
wherein the controller controls the display to display a guide UI for the food on a screen based on the obtained state information,
wherein the guide UI comprises at least one of a first UI element for providing a food state and a second UI element for providing recipe information of the food.

13. The electronic device of claim 9, further comprising:
a storage for storing a plurality of state change models by foods,
wherein the controller obtains a state change model of the food from among a plurality of prestored state change models based on the measured intensity and obtaining food state information by applying light intensity of a specific wavelength from among light intensities by wavelengths of the food to the obtained state change model.

14. The electronic device of claim 13, wherein the state change model is a model which is generated by accumulating light intensities measured from wavelength of light which is reflected by irradiating the food with light.

15. The electronic device of claim 9, further comprising:
a communicator configured to perform data communication with an external server,
wherein the controller controls the communicator to transmit the measured intensity to the external server and receive the state information of the food determined based on the measured intensity from the external server.

16. The electronic device of claim 9, wherein the state information comprises at least one of a type, ripening degree, and a content of nutrition of the food.

* * * * *